(12) United States Patent
Cavazza

(10) Patent No.: US 6,565,876 B1
(45) Date of Patent: May 20, 2003

(54) CARNITINE AND INOSITOL PHOSPHATE-CONTAINING COMPOSITION USEFUL AS DIETARY SUPPLEMENT OR DRUG

(75) Inventor: Claudio Cavazza, Rome (IT)

(73) Assignee: Sigma-Tau HealthScience S.p.A., Pomezia (IT)

( * ) Notice: Subject to any disclaimer, the term of this patent is extended or adjusted under 35 U.S.C. 154(b) by 0 days.

(21) Appl. No.: 09/720,099

(22) PCT Filed: Apr. 19, 2000

(86) PCT No.: PCT/IT00/00158

§ 371 (c)(1),
(2), (4) Date: Dec. 21, 2000

(87) PCT Pub. No.: WO00/64426

PCT Pub. Date: Nov. 2, 2000

(30) Foreign Application Priority Data

Apr. 22, 1999 (IT) .................................... RM99A0248

(51) Int. Cl.⁷ .............................................. A61K 47/00
(52) U.S. Cl. .................. 424/439; 424/400; 424/441; 424/451; 424/464; 424/484; 424/489
(58) Field of Search ................. 424/400, 439, 424/441, 451, 464, 484, 489

(56) References Cited

U.S. PATENT DOCUMENTS 5,626,849 A * 5/1997 Hastings et al. ............ 424/439
5,904,924 A * 5/1999 Gaynor et al. .......... 424/195.17

* cited by examiner

Primary Examiner—Thurman K. Page
Assistant Examiner—Charesse Evans
(74) Attorney, Agent, or Firm—Oblon, Spivak, McClelland, Maier & Neustadt, P.C.

(57) ABSTRACT

A composition is disclosed suitable for the prevention and/or treatment of cardiovascular and neurocerebral disorders, tissue anoxic forms, muscular energy deficits, inflammatory-type abnormalities, alterations of blood coagulation such as thrombosis, and tissue proliferation forms, that may take the form of a dietary supplement, dietetic support or of an actual medicine, which comprises as characterizing active ingredients: (a) propionyl L-carnitine or a pharmacologically acceptable salt thereof; and (b) an inositol phosphate, particularly the inositol hexaphosphate (IP6).

16 Claims, No Drawings

CARNITINE AND INOSITOL PHOSPHATE-CONTAINING COMPOSITION USEFUL AS DIETARY SUPPLEMENT OR DRUG

This application is a 371 of PCT/IT00/00158 filed Apr. 19, 2000.

The present invention relates to a composition for the prevention and/or treatment of cardiovascular and neurocerebral disorders, various tissue anoxic forms, energetic muscular deficits, inflammatory type-abnormalities, blood alterations of coagulation such as thrombosis, and tissue proliferation forms.

Accordingly, the composition may take the form and exert the action of a dietary supplement or of an actual medicine, depending upon the support or preventive action, or the strictly therapeutic action, which the composition is intended to exert in relation to the particular individuals it is to be used in.

More particularly the present invention relates to an orally, parenterally, rectally or transdermally administrable composition which comprises in combination as characterizing ingredients:

(a) propionyl L-carnitine or a pharmacologically acceptable salt thereof, optionally in combination with another "carnitine", where for "carnitine" is intended L-carnitine or an alkanoyl L-carnitine selected from the group comprising acetyl L-carnitine, butyryl L-carnitine, valeryl L-carnitine and isovaleryl L-carnitine or their pharmacologically acceptable salts; and (b) an inositol phosphate selected from the group comprising inositol monophosphate, inositol tetraphosphate, inositol pentaphosphate, particularly inositol hexaphosphate (IP6).

Both the carnitines and inositol hexaphosphate are well known for their important metabolic and pharmacological effects which have led to numerous favourable pharmacological and clinical findings.

As regards the carnitines, the role they play in the processes of β-oxidation of fatty acids and ATP synthesis is well known.

They are also endowed with important antioxidant activity, as demonstrated by their protective effect against the lipoperoxidation of the phospholipid cell membranes and against oxidative stress induced at myocardial and endothelial cell level. These biochemical effects of the carnitines are reflected in the favourable results obtained in clinical practice when they are used in the treatment of various forms of atherosclerosis, myocardial ischaemia, peripheral vasculopathy or diabetes.

Also as regards inositol hexaphosphate (IP6), numerous research studies of both biochemical and clinical nature have been published, which pinpoint its activities and use in the prevention and treatment of various pathological changes. Although the interest in this compound dates back many years, when the ability of certain plant seeds containing high percentages of IP6 to maintain their germinative capacity intact for very long periods of time was attributed to the antioxidant action of IP6, it was only recently that researchers began to detect its antithrombotic and antiatherosclerotic properties and its cardioprotective ability against damage caused by infarction as well as its ability to afford protection against the onset of tumour processes. These properties may be related in part to its high antioxidant capability and, on the other, to its ability to interfere with the release of cytokines and other products induced by the activation of receptors regulating cell transduction systems.

It is well known, in fact, that inositol hexaphosphate, IP6 or phytin, is present in high percentages in all tissues and cells. IP6 constitutes 1–5% by weight of many cereals and legumes, such as, for example, rice, wheat and soya, in which it constitutes approximately 50% of the phosphorus reserve. In clinical practice, the main areas in which IP6 has been successfully used relate above all to the treatment of hypercholesterolaemia and atherosclerosis, as well as hypercalcaemia and the resolution of kidney stones. Equally promising results have been achieved experimentally with its use in inhibiting ADP-induced platelet aggregation or the reperfusion damage of organs such as the heart.

Its incorporation in erythrocytes, moreover, leads to a greater availability of utilisable oxygen in those situations where the oxygen utilisation capability seems to be reduced, as in organ ischaemia, haemolytic anaemia, pulmonary insufficiency and erythrocytosis.

It should be recalled that the main factor underlying this activity of IP6 is its potent antioxidant action related above all to its iron-chelating ability.

As regards the vasculoprotective, neuroprotective and anti-anoxic effects of IP6, its incorporation in erythrocytes increases their stability to iron ions which can be released within the erythrocytes themselves and, moreover, by increasing their affinity for oxygen, make greater amounts of oxygen available at the level of tissues which have become anoxic.

Though the antioxidant effect of IP6 may account for its favourable activity at the metabolic and cardiovascular level, other mechanisms highlighted in recent studies have to be taken into consideration with regard to its anti-inflammatory, immunostimulant and anticancer properties.

IP6 and inositol pentaphosphate, IP5, are among the main inositol phosphates present in cells. In addition to modifying haemoglobin affinity for oxygen and acting as neurotransmitters, they perform an important function in the transduction of signals from the surface of the cell to its interior, in gene activation and in the formation of cytokines and factors regulating cell growth.

In the case of IP6's anticancer activity, the dephosphorylation of IP6 to IP5 and IP3 and a lowering of the pool of inositol phosphates characterised by lower phosphorylation, the prevalence of which regulates or inhibits cell growth, are postulated. IP6, moreover, is capable of blocking the activity of phosphatidylinositol-3-kinase (PI-3-kinase) and thus of blocking the Epidermal Growth Factor and the transduction of extracellular signals regulated by activation of protein kinase.

Another factor with a bearing on the anticancer activity of IP6 is that its dephosphorylation to IP3 is regarded as being related to the opening of the related calcium channels, an increase in which is not only a critical element in cell proliferation, but also an important factor in the induction of cell apoptosis. It has been found, moreover, that IP6 competes with the insulin Growth Factor receptors (IGF-II), and as a result it has been demonstrated that its gene overexpression gives rise to different tumour lines. IGF receptors, in any event, have been found to be important in initiating cellular hyperplasia.

In the anti-inflammatory, immunostimulant and anticancer action of IP6, then, two different mechanisms can be considered. One is peculiar to antioxidant agents which, like salicylic acid, inhibit the activation of gene transmission via the NK-kb-IkB system, and the other which, via the inositol phosphate pool, regulates growth factors. From the practical point of view, in the anticancer field, the use of IP6 has proved effective in inhibiting colon cancers induced in animals by azoxymethane with a dose-dependent activity.

Its use has also appeared to be equally effective in carcinoma of the breast induced by 7,12-dimethylbenzanthracene (DMBA) or by methyl-nitrosourea. Favourable results have also been obtained with the use of IP6 in cancers of the lung, prostate and liver. Tests conducted in human subjects, mainly on adenocarcinoma and leukaemia cells, have verified the anticancer efficacy of IP6.

It has now surprisingly been found that a combination composition containing as its characterising components:

(a) propionyl L-carnitine or one of its pharmacologically acceptable salts; and (b) an inositol phosphate, selected from the group consisting of inositol monophosphate, inositol tetraphosphate, inositol pentaphosphate and, particularly, inositol hexaphosphate (IP6) is extremely effective in the prevention and/or treatment of cardiovascular and neurocerebral disorders and of the various forms of tissue anoxia, inflammatory-type abnormalities, muscular energy deficits and tissue proliferation forms, as a result of the potent, unexpected synergistic effect exerted by its components.

It has also been found that, advantageously, component (a) may further comprise another "carnitine", selected from the group consisting of L-carnitine, acetyl L-carnitine, butyryl L-carnitine, valeryl L-carnitine and isovaleryl L-carnitine, or their pharmacologically acceptable salts or mixtures thereof, and that component (b) may additionally contain inositol.

The preferred weight ratio of component (a) to component (b) may range from 1:10 to 1:1.

Component (b) may be present in the compositions in the form of a vegetal product or an extract of vegetal products containing high percentages of inositol phosphates. Suitable vegetal products are, for example, bran and brown rice.

The composition according to the invention may be used both as a dietary supplement or nutritional supplement substance with a mainly preventive action, and as a medicine for the treatment of frank disease conditions.

The surprising synergistic effect which is achieved with the combination of "carnitines" and inositol phosphates, and particularly propionyl L-carnitine and IP6. has been confirmed by several pharmacological tests (some of which are described herein below) selected in such a way as to provide highly predictive indications with a view to the practical use of this composition both in the preventive/nutritional field and as a strictly therapeutic agent.

Toxicology Tests

Both L-carnitine and propionyl L-carnitine and inositol hexaphosphate (IP6) are known to be characterised by low toxicity and good tolerability. These favourable characteristics were confirmed by a single oral administration to rats and mice of doses of L-carnitine and IP6 corresponding to 1 g/kg and 750 mg/kg, respectively, and doses of propionyl L-carnitine and IP6 corresponding to 750 mg/kg and 500 mg/kg, respectively, without any toxic reaction or intolerance being detected. The intraperitoneal administration of 500 mg of propionyl L-carnitine and 300 mg of inositol hexaphosphate in rats was also well tolerated and no toxic effects were detected. These favourable low toxicity characteristics were also confirmed by the results of tests involving the daily oral administration of 300 mg/kg of propionyl L-carnitine together with 200 mg/kg of IP6 to rats for thirty consecutive days. At the end of these tests no reduction in the growth of the animals thus treated nor traceable changes either in haematocrit values or in the other blood chemistry variables, particularly serum glucose, BUN and cholesterol were detectable.

In addition, at autopsy no abnormalities of the main nor histological abnormalities of the main parenchymal tissues examined organs could be detected.

Anti-inflammatory Activity as Assessed by the Carrageenin Oedema Test

To assess the anti-inflammatory effect of the new composition the carrageenin oedema test was used, in which rat paws are injected with carrageenin.

The injection of 0.1 mL of 1% carrageenin solution (Sigma Chemical, St. Louis, Mo., USA) in the subplantar area of the rat's right paw induced marked oedema of the paw which reached its maximum intensity 4–5 hours after injection. The oedema was measured by mercury plethysmography at various different time intervals up to the fourth hour after carrageenin injection.

Both propionyl L-carnitine (250 mg/kg) and IP6 (250 mg/kg) were administered orally half an hour prior to the subplantar carrageenin injection. The results of this test (See Table 1) show that both propionyl L-carnitine and inositol hexaphosphate exerted a slight inhibitory action on the inflammatory reaction induced by carrageenin, whereas their combined use was capable of almost completely inhibiting the carrageenin-induced oedema, thereby demonstrating an unexpected and surprising synergistic effect of propionyl L-carnitine and inositol hexaphosphate.

TABLE 1

Anti-inflammatory activity as assessed by carrageenin oedema test

| | % inhibition after | | |
| --- | --- | --- | --- |
| | 1 h | 2 h | 4 h |
| Propionyl L-carnitine 250 mg/kg | — | 15 ± 0.3 | 8 ± 0.9 |
| IP6 250 mg/kg | 15 ± 1.1 | 20 ± 2.1 | 15 ± 0.6 |
| Propionyl L-carnitine 250 mg/kg + IP6 250 mg/kg | 00 ± 4.8 | 80 ± 7.1 | 50 ± 3.9 |

Anti-inflammatory Activity as Assessed by Collagen-induced Arthritis Test

Confirmation of the anti-inflammatory effects of the composition according to the invention was obtained using as a test collagen-induced type II arthritis according to the technique described by Trentham (Trentham D. R., *J. Exp. Med.*, 146:857, 1977). In this test, a group of mice were immunised by intradermal injection at the base of the tail of 100 μg of natural collagen emulsified in Freund complete adjuvant (Difco Labs., Detroit, USA).

After three weeks, the animals thus treated were again injected intraperitoneally with the same dose of emulsified collagen. The treatment with propionyl L-carnltine (200 mg/kg) or with inositol hexaphosphate (200 mg/kg) or with the two compounds in combination was administered orally from the day of collagen injection up to the end of the sixth week.

One group of animals received no treatment and served as a control group. The intensity of the oedema was assessed by assigning scores from 1 to 4. The results of this test also demonstrate a powerful synergism between propionyl L-carnitine and inositol hexaphosphate. In fact, while propionyl L-carnitine alone showed no inhibitory effect on the oedema induced by collagen and IP6 induced only a slight reduction (approximately 20%), when the two compounds were combined, the oedema inhibition was higher than 80%.

Anti-platelet Aggregation Activity

The anti-platelet-aggregation activity of the composition according to the invention was assessed in blood samples from healthy volunteers. The samples were treated with sodium citrate and centrifuged (145×g for 5 min at 22° C.) and the number of platelets was counted (CA 580=4 Platelet Counter–DelCon). This number was brought to a value of 300,000 platelets/mL by adding PPP (Platelet Poor Plasma), as necessary, obtained by centrifuging blood at 1,600×g for 10 min at 22° C.

The aggregating agent used was collagen (2.5 ng/mL, 5 ng/mL) and the aggregation induced was measured photometrically according to the method described by Born (Born G. V., *Nature*, 194:927, 1962). Platelet aggregation was measured in basal conditions and after 10 min of incubation with propionyl L-carnitine and IP6 alone or in combination.

The doses of propionyl L-carnitine used were 10 ng and 20 ng/mL, while the IP6 doses were 4 ng and 8 ng/mL.

The results of the tests indicate that whereas propionyl L-carnitine alone does not inhibit the aggregating action of collagen, IP6 alone reduces it to 40%. The combination of the two compounds, however, reveals complete inhibition of the aggregating activity (100%), which is an indicator of the effective synergistic action occurring between propionyl L-carnitine and IP6.

Anti-atherosclerotic Activity

The anti-atherosclerotic activity of the new composition was assessed in various groups of rats (male Wistar rats) which were administered an atherogenic diet for six weeks consecutively, consisting of 24% casein, 1% cholesterol, 15% cotton oil, 60% sugar and Vit. $D_2$ 200 m Ust/g diet according to the regimen proposed by Melinow (Melinow M. R., *Atherosclerosis*, 48:105, 1983). At the end of the sixth week of treatment, marked atherosclerotic vascular lesions had formed which were particularly pronounced at the abdominal aorta level. The severity of these lesions was evaluated by a morphometric method, measuring the thickness of the abdominal aorta and the intensity of the staining induced by Sudan IV with a progressive scoring system from 1 to 5. In these tests, the rats received daily administrations of 150 mg/kg of propionyl carnitine and 100 mg/kg of IP6, together with their atherogenic diets. The results of the examinations carried out on the rats thus treated showed that, whereas both propionyl L-carnitine and IP6 alone produce only a slight protective effect, the administration of the two compounds in combination almost totally inhibits the occurrence of atherosclerotic lesions as indicated by the morphometric examination and the Sudan IV staining, thus demonstrating, in this case, too, the powerful synergistic effect of combined propionyl L-carnitine and IP6.

Effects on Muscular Exercise

Since IP6, which is rich in phosphate groups, is a useful energy reserve, a series of tests were performed to establish whether its administration may increase the swimming endurance time in mice submitted to forced swimming in a rectangular tank full of water, according to the technique described by Zheng (Zheng R. L., *Acta Pharmacol. Sinica*, 14:47, 1993) and whether its effect could be enhanced by using it in combination with a carnitine, such as, for instance, propionyl L-carnitine. The tests were performed on various groups of animals treated with propionyl L-carnitine (200 mg/kg) or with IP6 (100 mg/kg) alone or with the two compounds in combination.

The compounds were administered orally on the three days preceding the test. In the animals thus treated, swimming endurance time was measured as compared to control animals. The mean swimming endurance time was slightly increased both in the rats treated with propionyl L-carnitine and in those treated with IP6 alone, whereas a marked lengthening of swimming time was found in animals treated with the combination of propionyl L-carnitine and IP6, thus demonstrating an evident synergistic effect (see Table 2).

In another series of tests, the effect of the combination of propionyl L-carnitine and IP6 on forced muscular exercise was evaluated, which, as is known, can generate reactive oxygen species (ROS), inflammation and damage to muscular structures.

Forced muscular exercise was tested in various groups of rats by making them run on a moving belt at controlled speed and angle of tilt, as described by Li (Li J. X., *Acta Pharmacologica Sinica*, 20:126, 1999) and Husain (Husain K., Pathophysiology, 4:69, 1997). The animals were made to run on an approximately 5° slope and at a belt speed of 28 m/min. The animals' stamina reached the point of exhaustion after approximately 85 min of exercise.

The test was carried out in groups of animals which, during the three days preceding exercise, received 200 mg/kg of propionyl L-carnitine or 100 mg/kg of IP6 alone or in combination. Five and thirty minutes, respectively, after the end of exercise, samples of gastrocnemius muscle were taken from the sacrificed animals and used for measuring the malondialdehyde (MDA) content as a marker for the level of lipoperoxidation by means of reaction with thiobarbituric acid according to the method described by Ohkawa (Ohkawa H., *Anal. Biochem.*, 95:351, 1979).

As apparent from the results given in Table 3, both propionyl L-carnitine and IP6 alone were capable of reducing the levels of muscle lipoperoxidation in muscle homogenate as detected by the lower increase in MDA, which, by contrast, was very marked in the control mice five minutes after the end of exercise. The combination of propionyl L-carnitine and IP6, on the other hand, affords almost total protection against lipoperoxidation in the muscles of treated animals, thus demonstrating in this case, too, the synergistic effect of propionyl L-carnitine and IP6.

TABLE 2

Swimming endurance test

| Treatment | Swimming time (min) |
| --- | --- |
| Controls | 98 ± 15 |
| Propionyl L-carnitine | 116 ± 19 |
| IP6 | 136 ± 16 |
| Propionyl L-carnitine + IP6 | 184 ± 22 |

TABLE 3

Muscle fatigue tests

| | MDA content in muscle [nmol · $g^{-1}$ (WW)] | |
| --- | --- | --- |
| Treatment | after 5 min | after 30 min |
| Controls | 234 ± 9 | 225 ± 11 |
| Propionyl L-carnitine | 210 ± 10 | 212 ± 14 |
| IP6 | 200 ± 16 | 205 ± 8 |
| Propionyl L-carnitine + IP6 | 175 ± 12 | 181 ± 12 |

Effects on Neuronal Hypoxia

To assess the protective activity of the composition according to the invention on hypoxia-induced damage at the neuronal level, tests were performed on cultures of chick cerebral neurons in which the reduction in cell respiration was induced by introducing NaCN into the cultures. The energy metabolism of the neuronal cultures was assessed by measuring the ATP concentrations present in the cultures without treatment or in cultures to which propionyl L-carnitine or IP6 were added at the doses of 100 and 50 mg/L, respectively. The chick cerebral neuron cultures were prepared according to the technique described by Pettman (Pettman B., *Nature*, 281:378, 1979). Cytotoxic hypoxia was induced by adding NaCN to the culture medium to a final concentration of 1 mmol/L. After 120 min the medium was replaced by an NaCN-free medium, and the metabolism of the cells was blocked by washing with an iced buffer solution. The ATP assay was performed according to the procedure described by Werner (Werner A. J., *Chromatogr. Biomed. Appl.*, 421:257, 1987).

The results of these tests are shown in Table 4. ATP measurement shows that ATP levels are substantially reduced by anoxia and remain low even after thirty-minute reoxygenation, whereas, when propionyl L-carnitine or IP6 are present alone or in combination, a lesser reduction of ATP levels is observed as well as more rapid restoration of ATP levels.

TABLE 4

Effect on neuronal hypoxia

| Treatment | ATP nmol g protein after reoxygenation time | |
|---|---|---|
| | 0 | 30 min |
| Controls | 9.2 ± 0.9 | 14.4 ± 1.2 |
| Propionyl L-carnitine | 11.1 ± 1.6 | 16.3 ± 2.2 |
| IP6 | 12.4 ± 2.1 | 16.9 ± 1.9 |
| Propionyl L-carnitine + IP6 | 15.8 ± 2.4 | 23.7 ± 2.3 |

Antiproliferative Activity

In view of the numerous research studies regarding the preventive chemotherapeutic anticancer activity demonstrated experimentally by IP6, particularly against cancers of the colon and breast, the anti-proliferative activity of the composition according to the invention was assessed in relation to the proliferation of skin tissue experimentally induced in mice by subcutaneously injecting teleocidin which, like the phorbolmyristates, is capable of causing cancer-like proliferative skin abnormalities (Fujiki A., *Biochem. Biophys. Res. Comm.*, 90:976, 1979).

Since the skin reactions induced by teleocidin are accompanied by an increase in ornithine decarboxylase activity, this enzyme can be regarded as a marker for the proliferative reaction and its differing degrees of severity.

For these tests, teleocidin was injected subcutaneously into the depilated backs of mice at the dose of 5 µg/mouse.

One week prior to the injection of teleocidin, the various groups of animals received oral administrations of propionyl L-carnitine (200 mg/kg) or IP6 (100 mg/kg) or the two compounds in combination. Five hours after injection of teleocidin, the ornithine decarboxylase assay was carried out on homogenised epidermis of the animals treated according to the method described by O'Brien (O'Brien T. G., *Cancer Res.* 42:2841, 1982).

The evaluation of the ornithine decarboxylase concentration in protein of the epidermal extract was done according to the technique described by Lowry (Lowry O. H., *J. Biol. Chem.*, 193:265, 1951). As apparent from the results in Table 5, the increase in ornithine decarboxylase activity induced by telcocidin was significantly reduced by prior administration of propionyl L-carnitine or IP6 alone. However, when the two compounds were used in combination, the reduction in ornithine decarboxylase activity became marked and highly significant.

TABLE 5

Antiproliferative activity

| Treatment | Ornithine decarboxylase activity nMol of $CO_2$/60 min/mg protein |
|---|---|
| Controls | 0.055 ± 0.004 |
| Teleocidin | 2.6 ± 0.4 |
| Propionyl L-carnitine | 2.1 ± 0.2 |
| IP6 | 1.95 ± 0.2 |
| Propionyl L-carnitine + IP6 | 0.58 ± 0.9 |

What is meant by pharmacologically acceptable salt of L-carnitine or alkanoyl L-carnitine is any salt of these active ingredients with an acid that does not give rise to unwanted toxic or side effects. These acids are well known to pharmacy experts.

Non-limiting examples of suitable salts are the following: chloride; bromide; iodide; aspartate, acid aspartate; citrate, acid citrate; tartrate; phosphate, acid phosphate; fumarate; acid fumarate; glycerophosphate; glucose phosphate; lactate; maleate, acid maleate; orotate; oxalate, acid oxalate; sulphate, acid sulphate, trichloroacetate, trifluoroacetate and methanesulphonate.

A list of FDA-approved pharmacologically acceptable salts is given in *Int. J. of Pharm.* 33, (1986), 201–217; this latter publication is incorporated herein by reference.

The composition according to the invention may also comprise vitamins, coenzymes, minerals substances and antioxidants.

Appropriate excipients to be used to prepare the compositions having regards to the specific route of administration, will be apparent to the pharmacy and food industry experts.

Illustrative, non-limiting examples of compositions according to the invention are reported hereinbelow.

| | |
|---|---|
| 1) Propionyl L-carnitine | 250 mg |
|    Inositol hexaphosphate | 250 mg |
| 2) L-carnitine | 150 mg |
|    Propionyl L-carnitine | 150 mg |
|    Inositol hexaphosphate | 300 mg |
| 3) Carnitine mixture | 300 mg |
|    (L-carnitine 75 mg, acetyl L-carnitine 75 mg, propionyl L-carnitine 75 mg, isovaleryl L-carnitine 75 mg) | |
|    Inositol hexaphosphate | 300 mg |
| 4) Propionyl L-carnitine | 200 mg |
|    Inositol hexaphosphate | 200 mg |
|    Inosine | 100 mg |
| 5) Carnitine mixture | 200 mg |
|    (L-carnitine 50 mg, acetyl L-carnitine 50 mg, propionyl L-carnitine 50 mg, isovaleryl L-carnitine 50 mg) | |
|    Inositol phosphate complex | 200 mg |
|    (inositol hexaphosphate 100 mg, inositol pentaphosphate 50 mg, inositol tetraphosphate 50 mg) | |
|    Inosine | 100 mg |
| 6) Acetyl L-carnitine | 200 mg |
|    Propionyl L-carnitine | 200 mg |
|    Inositol hexaphosphate | 400 mg |
|    Inosine | 200 mg |
| 7) Propionyl L-carnitine | 200 mg |
|    Inositol hexaphosphate | 200 mg |
|    Inosine | 100 mg |
|    Coenzyme $Q_{10}$ | 20 mg |

-continued

| | |
|---|---|
| Vit. E | 5 mg |
| β-carotene | 10 mg |
| Bioflavonoids | 25 mg |
| Vit. C | 25 mg |
| Selenium | 50 mg |
| Plant fibres | 50 μg |
| Magnesium stearate | 5 mg |
| 8) Propionyl L-carnitine | 200 mg |
| Inositol hexaphosphate | 200 mg |
| Inosine | 100 mg |
| Creatine | 100 mg |
| Vit. $B_1$ | 1 mg |
| Vit. $B_2$ | 3 mg |
| Vit. $B_6$ | 5 mg |
| Nicotinamide | 5 mg |
| Vit. E | 5 mg |
| β-carotene | 10 mg |
| Vit. $B_{12}$ | 2 μg |
| Folic acid | 700 μg |

What is claimed is:

1. A composition which comprises:
   (a) propionyl L-carnitine or a pharmacologically acceptable salt thereof; and
   (b) an inositol phosphate.

2. The composition of claim 1, wherein the inositol phosphate is selected from the group consisting of inositol monophosphate, inositol tetraphosphate, inositol pentaphosphate and inositol hexaphosphate (IP6).

3. The composition of claim 1, wherein the ingredient (a) further comprises at least one "carnitine" selected from the group consisting of L-carnitine, acetyl L-carnitine, butyryl L-carnitine, valeryl L-carnitine, isovaleryl L-carnitine and their pharmacologically acceptable salts.

4. The composition of claim 1, wherein ingredient (b) further comprises inositol.

5. The composition of claim 1, wherein the weight ratio (a):(b) is from 1:10 to 1:1.

6. The composition of claim 1, wherein the ingredient (b) is a vegetable product or extract of vegetable products containing same.

7. The composition of claim 6, wherein the vegetable product is bran or brown rice and/or their extracts.

8. The composition of claim 1, wherein the propionyl L-carnitine is present as a pharmacologically acceptable salt thereof selected from the group consisting of chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; orotate; acid oxalate; sulphate, acid sulphate; trichloroacetate; trifluoroacetate and methanesulphonate.

9. The composition of claim 1, which further comprises at least one of vitamins, coenzymes, mineral substances and antioxidants.

10. The composition of claim 1, which is orally administrable, in the form of a dietary supplement.

11. The composition of claim 1, which is orally, parenterally, rectally or transdermally administrable, in the form of a medicament.

12. A method for the prevention of tissue anoxic forms, cardiac or nervous disturbances, muscular energy deficits, asthenia and fatigue, inflammatory-type abnormalities, or tissue proliferation forms comprising administering the dietary supplement of claim 10 to a patient in need thereof.

13. A method for the therapeutic treatment of free radical induced-pathologies, for the treatment of cardiovascular or cerebral disorders due to tissue anoxia or ageing, alterations of blood coagulation, inflammatory-type abnormalities, muscular energy deficits accompanied by asthenia and fatigue or as adjuvant in the treatment of tissue proliferation forms comprising administering the medicament of claim 11 to a patient in need thereof.

14. The method of claim 12, wherein the dietary supplement is administered in the form of tablets, pills, capsules, granulates or syrups.

15. The method of claim 13, wherein the medicament is administered in the form of tablets, pills, capsules, granulates, syrups, suppositories, vials or drops.

16. The composition of claim 1, wherein the ingredients (a) and (b) are present in synergistic amounts.

* * * * *